United States Patent
Rossi et al.

(10) Patent No.: US 6,583,287 B1
(45) Date of Patent: Jun. 24, 2003

(54) PROCESS FOR THE PRODUCTION OF PAROXETINE

(75) Inventors: Renzo Rossi, Pisa (IT); Stefano Turchetta, Rome (IT); Maria Donnarumma, Latina (IT)

(73) Assignee: Recordati S.A. Chemical and Pharmaceutical Company (CH)

( * ) Notice: Subject to any disclaimer, the term of this patent is extended or adjusted under 35 U.S.C. 154(b) by 0 days.

(21) Appl. No.: 09/890,414

(22) PCT Filed: Feb. 22, 2000

(86) PCT No.: PCT/EP00/01430

§ 371 (c)(1),
(2), (4) Date: Jul. 30, 2001

(87) PCT Pub. No.: WO00/50422

PCT Pub. Date: Aug. 31, 2000

(30) Foreign Application Priority Data

Feb. 23, 1999 (IT) .......................................... MI99A0364

(51) Int. Cl.$^7$ .............................................. C07D 405/12
(52) U.S. Cl. ........................ 546/197; 546/236; 546/240
(58) Field of Search ................................ 546/197, 236, 546/240

(56) References Cited

U.S. PATENT DOCUMENTS 4,994,590 A    2/1991    Takaya et al. ................. 556/21

FOREIGN PATENT DOCUMENTS

| EP | 0366390 | 5/1990 |
|----|---------|--------|
| WO | WO9209552 | 6/1992 |
| WO | WO9322284 | 11/1993 |
| WO | WO9636636 | 11/1996 |
| WO | 98/01424 | * 1/1998 |

OTHER PUBLICATIONS

March, Jerry "Advanced Organic Chemistry" 3$^{rd}$ ed. John Wiley & Sons p. 107 1985.

Willcocks, K. et al. The synthesis of [$^{14}$C]–3S, 4R–4–(4–fluorophenyl)–3(3,4–methylenedioxyphenoxymethyl) piperidine hydrochloride (BRL 29060A), and mechanistic studies using carbon–13 labelling. Journal of Labelled Compounds and Radio Pharmaceuticals vol. XXXIII, No. 8, John Wiley & Sons pp. 783–794, 1993.

* cited by examiner

*Primary Examiner*—Ceila Chang
(74) *Attorney, Agent, or Firm*—Morgan & Finnegan, L.L.P.

(57) ABSTRACT

A process for the production of paroxetine is described, wherein N-substituted derivatives of 4-(p-fluorophenyl)-3-hydroxymethyl-1,2,3,6-tetrahydropyridine are treated according to the following sequence of reactions: (a) hydrogenation catalyzed by transition metal complexes with chiral diphosphinic ligands; (b) —OH derivatisation and nucleophilic substitution, the substituent being sesamol; (c) N-dealkylation. The process is highly stereospecific and brings about the formation of intermediates enriched with the desired isomeric components, which are converted into paroxetine in quantitative yields.

14 Claims, 4 Drawing Sheets

PROCESS FOR THE PRODUCTION OF PAROXETINE

FIELD OF THE INVENTION

The field of the present invention is the synthesis of optically active compounds. A highly stereospecific process for synthesis of paroxetine is described herein.

PRIOR ART

Paroxetine is a compound widely used for the treatment of depression. The structural formula of this compound is as follows (I):

The molecule of formula (I) contains two chiral centres on the piperidinic ring, in position 3 and 4, respectively. Of the four possible isomers, only the isomer having absolute configuration 3S, 4R, known as 4R-trans-4-(p-fluorophenyl-3-{[3,4-(methylenedioxy)phenoxy]methyl}piperidine, is pharmacologically active. Therefore, the processes for synthesis of paroxetine must result in the formation of the 4-(p-fluorophenyl-3-{[3,4-(methylenedioxy)phenoxy]methyl}piperidinic structure, exclusively in the aforesaid conformation, 3S, 4R (or 4R-trans).

Some processes for synthesis of paroxetine known to the art are based on the formation of an intermediate of formula (II)

where R represents an alkyl group. Starting from this intermediate, the product of formula (I) is obtained by: (i) reduction of the piperidinic double bond, (ii) alkylation of the oxygen of the hydroxymethyl group, and (iii) removal of the alkyl group R bound to the nitrogen. In order to obtain the product (I) with the pharmacologically active conformation, the process requires the isolation of specific isomers from the corresponding racemic mixtures and the treatment of the same until obtaining derivative (I) with the desired conformation.

For example, patent application WO-A-9636636 discloses the synthesis of 4-arylpiperidine, wherein a derivative of formula (II) is separated into the two optical isomers by crystallisation with optically active salts. The two optical isomers are then separately converted into paroxetine. Therefore, the process requires separate and independent synthesis routes for isomers treatment and, consequently, can hardly be scaled up to commercial size.

According to another process (J. Labelled Compounds Radiopharm., 1993, 8, 785), the derivative of formula (II) is hydrogenated and alkylated as per the above scheme; subsequently the diastereoisomers are isolated by chromatography while the enantiomers are separated by crystallisation with L-(+)-tartaric acid. The (−)-trans isomer is finally converted into paroxetine by N-dealkylation. In this case, two distinct isomers separation cycles are required, resulting in a considerable loss of product in the form of undesired isomer. Consequently, this process too can hardly be applied to commercial-scale production.

The process disclosed in patent application WO-A-9322284 is based on the stereospecificity of esterase-catalysed reactions. In this case, the enzyme brings about the formation of a trans carboxylic precursor, wherefrom the (+)-trans and (−)-trans forms are separated by conventional methods. The latter form further undergoes reduction and alkylation to give paroxetine. The advantage of this process is a high stereospecificity; its disadvantages are the enzyme cost and instability. The aforesaid reactions are usually slow and must be carried out under precise pH and temperature conditions.

In brief, the separation processes known to the art cause a considerable loss of product in the form of isomers with undesired configuration or require separate process cycles for the conversion of said isomers. In particular, the processes known to the art entail the resolution of racemic mixtures in which the dextro- and levorotatory components are present in substantially similar proportions, with the result that approx. half of the resolved product is to be discarded or independently converted into the desired form.

Therefore, the need for developing highly stereospecific processes for the synthesis of paroxetine, whereby the desired isomers are obtained in high yields, is felt. Particularly urgent is the need for processes not involving isomer resolution cycles and not requiring separate ad hoc treatments of the single isomers.

DESCRIPTION OF THE FIGURES

FIGS. 1A–1H are examples of chiral diphosphinic ligands:

DETAILED DESCRIPTION OF THE INVENTION

It is an object of the present invention to provide a process for the synthesis of paroxetine. The process comprises the following steps:

a) hydrogenation of a compound of formula (II), where R is a group selected from $(C_1-C_5)$alkyl, $(C_1-C_5)$ carboxyalkyl, an optionally substituted phenyl, an optionally substituted benzyl, said hydrogenation being catalysed by a complex of a transition metal with chiral diphosphinic ligands, resulting in a 4R-enantiomerically enriched compound of formula (III):

b) reaction of the compound of formula (III) with a reagent capable of transforming the —OH group into a leaving group, followed by nucleophilic substitution with sesamol (3,4-methylenedioxyphenol), resulting in a 4R-enantiomerically enriched derivative of formula (IV);

c) N-dealkylation of compound (IV), resulting in paroxetine (I):

In formula (II), R preferably represents an ethyl group. Should R represent an optionally substituted phenyl or benzyl, the substituent is preferably a $(C_1-C_5)$alkyl.

The compound of formula (III) obtained in step a) contains two asymmetry centres on the piperidinic ring, in position 3 and 4, respectively. Said product is obtained as a mixture of 4R-enantiomerically enriched cis (IIIa) and trans (IIIb) isomers, where each of the two isomers (cis and trans) is mainly present in the form having absolute configuration R on the carbon atom in position 4 of the piperidinic ring. By the term "4R-enantiomerically enriched" it is meant an overall enantiomeric excess (also called overall "ee") of at least 80%. The enantiomeric excesses are calculated as described in J. March, "Advanced Organic Chemistry", 3rd Ed., Chapter 4, p. 107 (John Wiley & Sons) (1985).

The catalysts to be used in hydrogenation (step a) are compounds belonging to the class of transition metal complexes with chiral diphosphinic ligands. Said catalysts are responsible for the reaction stereospecificity and allow the obtainment of 4R-enantiomerically enriched derivative of formula (III). Members of this class are all the transition metal complexes with chiral diphosphinic ligands. In said complexes, the metal coordinates to the chiral ligand to give a chiral complex capable of catalysing a highly stereospecific hydrogenation of the double bond. Preferred transition metals are ruthenium, rhodium and iridium.

Figure 1A:
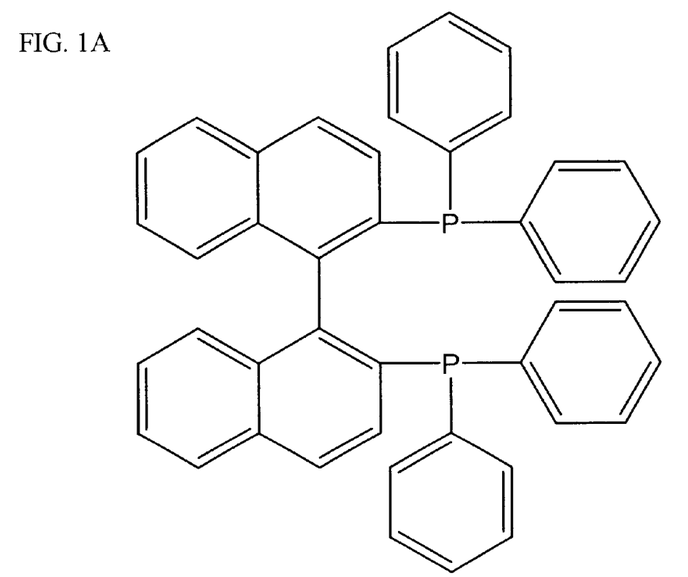
FIG. 1A: BINAP
Figure 1B:
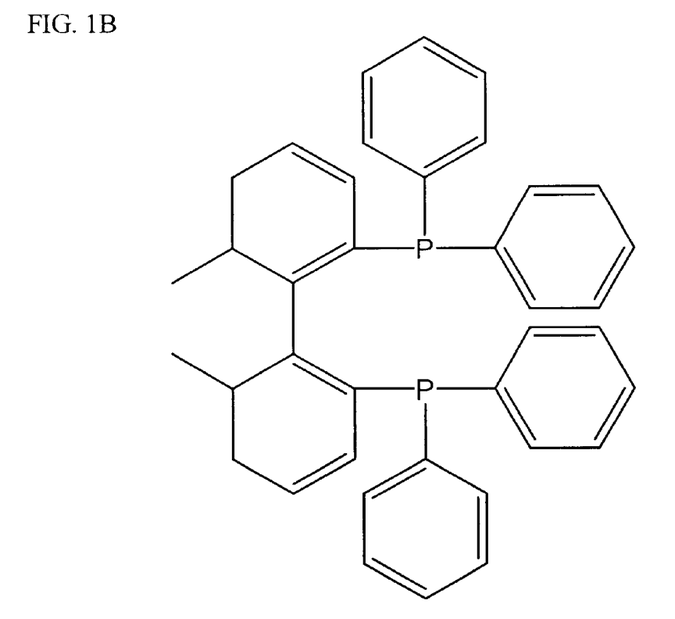
FIG. 1B: BIPHEMP
Figure 1C:
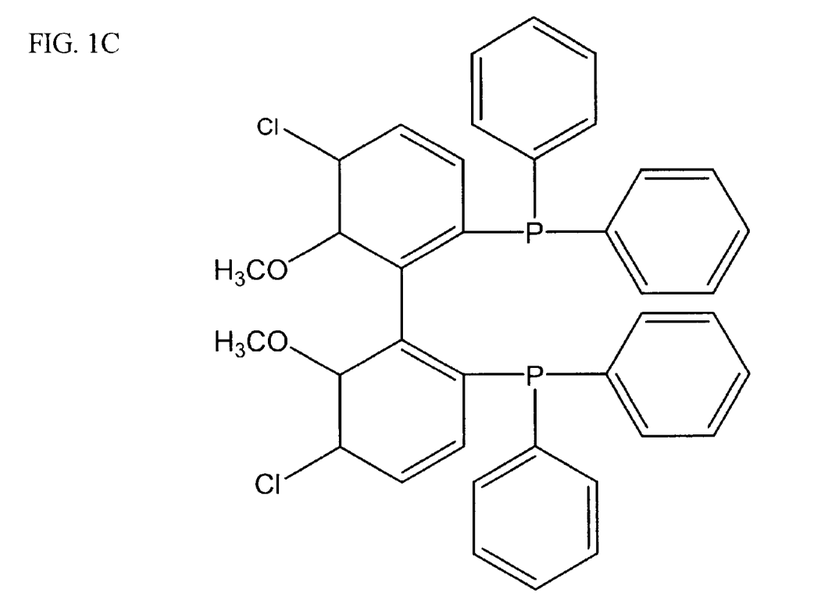
FIG. 1C: (5,5'-dichloro-6,6'-dimrthoxy-diphenyl-2,2'-diyl)-bis-(diphenylphosphine)
Figure 1D:
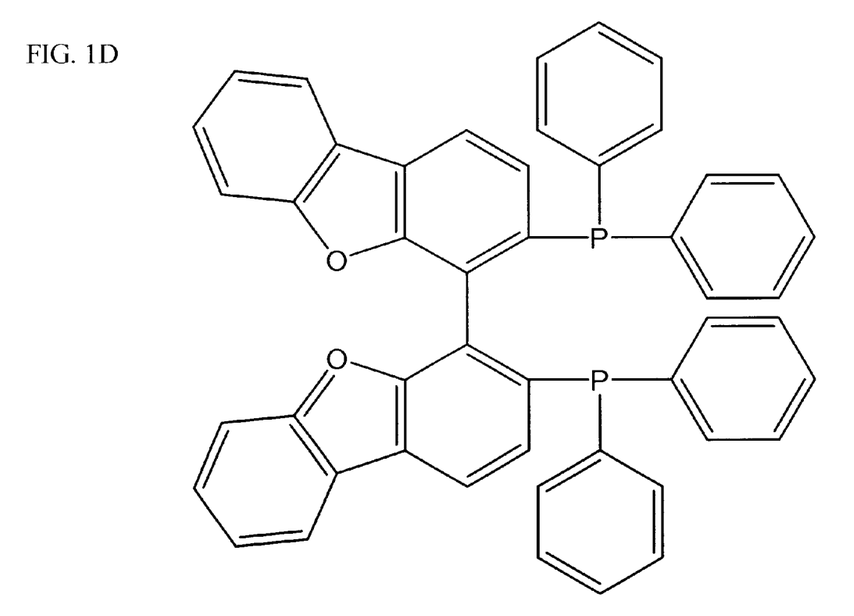
FIG. 1D: (bis-4,4'-dibenzofuran-3,3'-yl)-bis diphenylphosphine
Figure 1E:
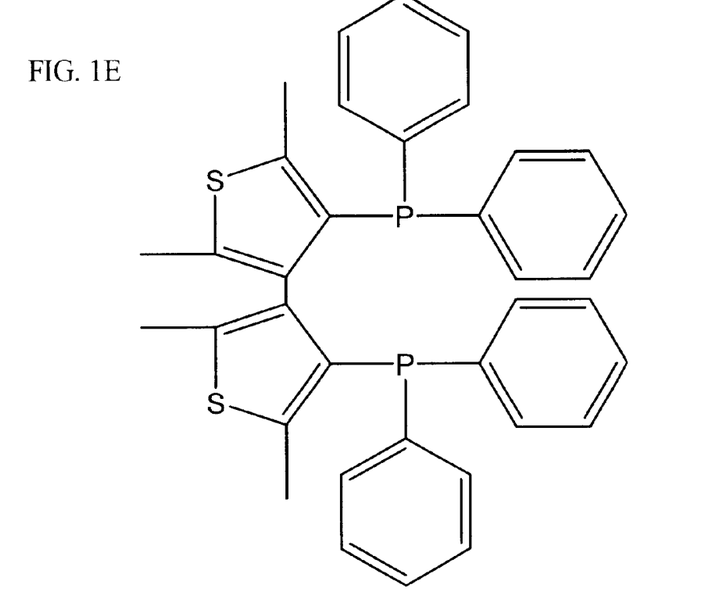
FIG. 1E: 4,4'-bisdiphenylphosphine-2,2',5,5'-tetramethyl-3,3'-dithiophene
Figure 1F:
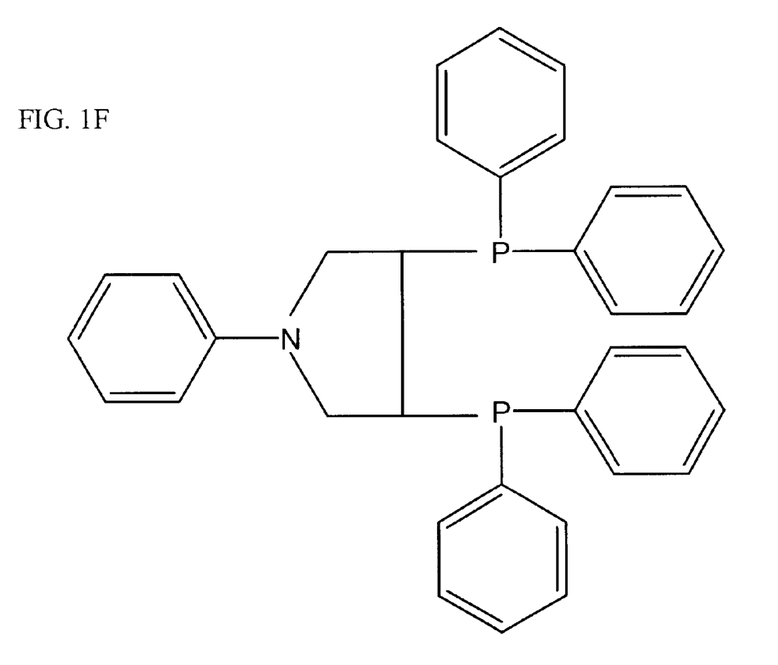
FIG. 1F: PYRPHOS
Figure 1G:
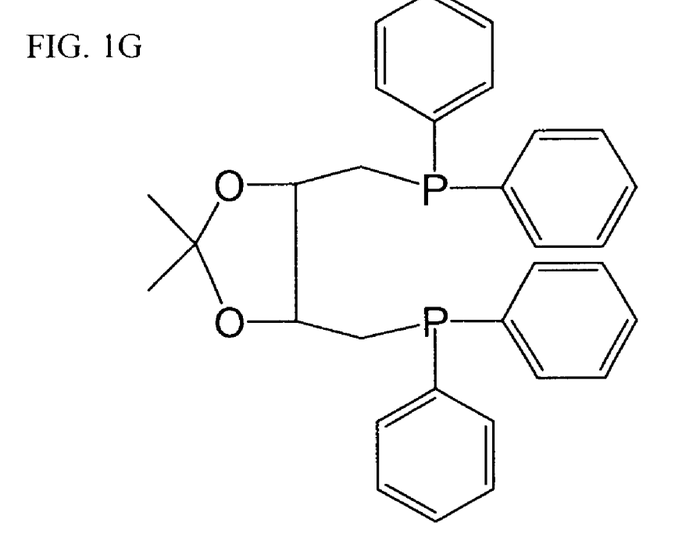
FIG. 1G: DIOP
Figure 1H:
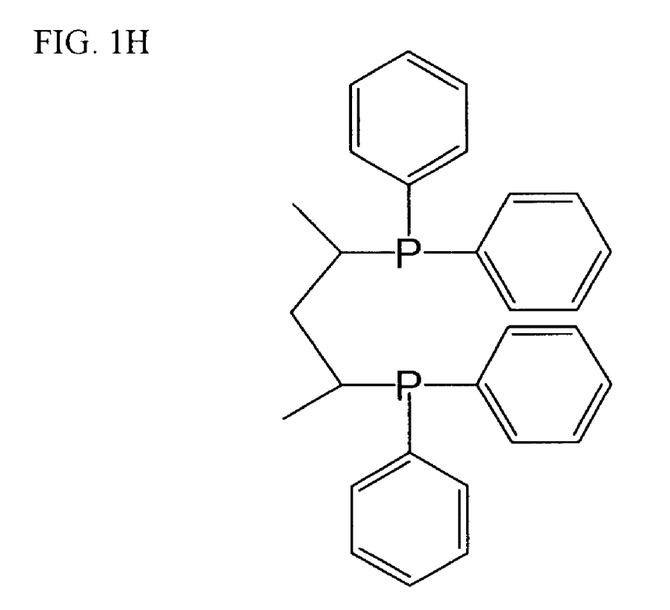
FIG. 1H: BDPP

Examples of chiral diphosphinic ligands are the compounds belonging to the formulas indicated in FIGS. 1A–1H.

Examples of transition metal complexes with chiral diphosphinic ligands are the compounds of formula $RuX_l(L)_m[BINAP]Y_n$, described in the patent application EP-A-366390, or the compounds of formula described in EP-A-245959. Preferred complexes are the compounds: {RuCl(p-cymene)[BINAP]}Cl; RuHCl[BINAP]$_2$; Ru$_2$Cl$_4$[(BINAP]$_2$NEt$_3$; Ru[BINAP](OAc)$_2$; Ru[BINAP](CF$_3$CO$_2$)$_2$, and the compounds of formulas RuCl-p-cymene RuCl-p-cymene RuCl-p-cymene and the compounds of formula {Ru(p-cymene)X[BINAP]}⁺X⁻, where X represents a halogen atom, such as the compound {Ru(p-cymene)Cl[BINAP]}⁺Cl⁻.

As mentioned above, all these complexes are chiral; depending on each complex, only one of the chiral forms, e.g. (S)BINAP or (R)BINAP generates in the 4R-enriched product: this form is not determinable a priori, but can be easily selected by performing a screening hydrogenation test of compound (II), with the ligand in one enantiomeric form (e.g. (S)-BINAP) and checking whether the hydrogenated product is enantiomerically enriched in the 4R or 4S form: in the synthesis of paroxetin the enantiomeric ligand resulting in the 4R-enriched form will have to be used.

The transition metal complexes with chiral diphosphinic ligands can be used as such or in a supported form e.g. onto a polymeric matrix.

Hydrogenation is typically carried out in alcoholic and/or halogenated solvents at 1 to 150 atm and 60° C. to 150° C., more preferably at 5 to 15 atm and 100° C. to is 130° C., and most preferably at 10 atm and 120° C. Non limitative examples of the above solvents are ethanol, methanol, n-propanol, isopropanol, n-butanol, isobutanol, cyclohexanol, dichloromethane, dichloroethane, trichloroethane, carbon tetrachloride.

According to a more specific embodiment of the present invention, it is possible to obtain the hydrogenated product (III), substantially free from the 4S-form: by this expression it is meant that each of the (IIIa) and (IIIb) isomers is present with an own enantiomeric eccess of the 4R form of at least 95%; the overall enantiomeric excess (IIIa)+(IIIb) is also ≧95%. This realization is most preferred since it minimizes or substantially avoids any product loss in the form of undesired enantiomer, thus enhancing the simplicity, selectivity and economic profitability of the process. The reaction conditions are substantially those described above, i.e. from 1 to 150 atm and 60° C. to 150° C., more preferably at 5 to 15 atm and 100° C. to 130° C., and most preferably at 10 atm and 120° C.; however in order to obtain the above mentioned enantiomeric eccess of at least 95%, the solvent is to be chosen among: dichloromethane, n-propanol, isopropanol, isobutanol, cyclohexanol, and their mixtures, and the complex is to be selected from {RuCl(p-cymene) [(S)-BINAP]}Cl, RuHCl[(S)-BINAP]₂, Ru₂Cl₄[(S)-BINAP]₂(NEt₃). As a further advantage, when the hydrogenation reaction is catalysed, by {RuCl(p-cymene)[(S)-BINAP]}Cl, in the presence of isopropanol as a solvent, the aforementioned substantial enantiomeric purity is associated with an extremely favourable conversion rate of product (II) to (III), [100% in 5 hrs reaction time], which element further adds significantly to the above discussed advantages.

The compound (III) resulting from step a. is used as a cis-trans mixture (IIIa+IIIb) in the next reaction (step b). Step b. requires firstly to transform the —OH group of compound (III) into a leaving group by reaction with an appropriate reagent. Preferred reagents for this operation are tosyl chloride, methanesulphonyl chloride, benzenesulphonyl chloride. Said reagents are added to compound (III), at a temperature comprised between −20° C. and +25° C. (preferably 0° C.–5° C.) in the presence of an inert solvent (e.g. a aromatic or aliphatic hydrocarbon, such as toluene), and of a basic compound (e.g. an organic base like triethylamine or an inorganic base or basic salt). This reaction results in an activated intermediate of formula:

(X = Bs / Ts / Ms)

This product, by addition of sesamol (3,4-methylenedioxyphenol) in a basic medium, is transformed into a 4R-enantiomerically enriched compound of formula (IV), mainly in the trans form. Sesamol, as a liquid mixture with an alcoholic solvent, preferably 4-methylpentan-2-ol, is added in a 1:1 equiv. ratio referred to benzenesulphonyl chloride or methanesulphonyl chloride or tosyl chloride. The mixture is conveniently heat-refluxed preferably for a period of 2 to 4 hrs to give 4R-enantiomerically enriched trans-diastereoisomer (IV) and a minor quantity of cis diastereoisomer, which is eliminated by crystallisation.

The product (IV) is obtained mainly in the trans form, while the 4R enantiomeric enrichment previously produced is almost completely maintained, as shown by the HPLC analysis data presented in the experimental part.

Step c) consists in the elimination of the alkyl group R bound to the nitrogen atom. The reaction is performed by techniques known to the art. According to a preferred embodiment, the product (IV) is mixed with phenylchloroformate in CH₂Cl₂ and allowed to react for 1 to 6 hours at room temperature. At the end, the carbamic derivative of the following formula is obtained:

which is then hydrolysed with KOH.

At the end of step c), a compound of formula (V)

is obtained, which is enantiomerically enriched in its 4R form (paroxetine). If present, the minor isomeric portion having 4S configuration is eliminated by crystallization. Pure paroxetine (I) is thus obtained. The compounds of formula (II) used as reagents in step a) of the process described herein may be easily obtained by various techniques known to the art, e.g. by allowing 1-methyl-4-fluorostyrene to react with formaldehyde and ethylamine hydrochloride, as disclosed in WO-A-9636636.

Alternatively, compounds of formula (II) may be obtained as shown in the following scheme:

4-Fluorobromobenzene and magnesium are allowed to react to give 4-fluorophenylmagnesium bromide (VI), to which 1-alkyl-4-piperidone is added. The resulting product is 1-alkyl4-(p-fluorophenyl)-4-hydroxypiperidine (VII), which is dehydrated in position 3–4 of the piperidinic ring by heat-reflux with aqueous $H_2SO_4$, to obtain 1-alkyl-4-(p-fluorophenyl)-1,2,5,6-tetrahydropyridine (VII). This product is finally converted into the product of formula (II) by addition, in the same reaction medium, of aqueous formaldehyde (Prins's reaction).

In the process of the invention, catalytic hydrogenation a) largely increases the percentage amount of enantiomers useful for paroxetine (4R) formation, and reaction b) allows the use of compound (III) in both cis and trans forms. It follows that the quantity of product to be discarded as isomerically undesired is very low and, consequently, the yield to paroxetine is high.

Furthermore, an advantage of the present invention is that it avoids following independent synthetic routes for cis and trans isomers, as is instead required by the aforementioned processes known to the art.

Another advantage of the present invention is that the aforesaid enantiomeric excesses may be obtained at moderate pressure (5 to 15 atm): under these conditions the process may be easily scaled up to commercial size.

A still further advantage of the present invention is that high enantiomeric excesses may be obtained also with low catalyst/substrate ratios, i.e. ranging from 1/200 to 1/1000. The use of low quantities of catalyst favours low process investment.

The following examples are shown by way of indication, not of limitation, of the present invention.

EXPERIMENTAL PART

A) Synthesis of 1-Ethyl-4-(p-fluorophenyl)-4-hydroxy-piperidine (VII) [R=Et]

A ca. 0.9 M solution of 4-fluorophenylmagnesium bromide (1.0 equiv., 0.31 moles) prepared as usual from magnesium and 4-fluorobromobenzene in THF was titrated, cooled to 0° C., and added dropwise over approx. 45 min. with a clear solution of commercial 1-ethyl-4-piperidone (1 equiv., 0.31 moles) in THF (60 ml).

Once the addition had been completed, the reaction was maintained at room temperature for 1 hr.

The reaction mixture was cooled to 5° C. and added with 360 ml of a 20% $NH_4Cl$ solution. At the end of the addition, the phases were separated and the organic phase was evaporated to dryness. The aqueous phase was extracted with two portions of 250 ml of toluene. The residue was evaporated and the toluenic phases were joined and washed with 420 ml of a 20% $NH_4Cl$ solution.

The organic phase was concentrated and cooled. After filtration of the precipitate thus obtained, 40.9 g of a pale yellow solid product were isolated. Its HPLC analysis (Column Symmetry Shield RP8, Eluent acetonitrile:buffer= 90:10 ($KH_2PO_4$ 0.025 M at pH 2.5 with $H_3PO_4$), flow 1/ml/min, Detector UV 215 nm) showed assay of 98%, and purity >98%, with a yield of 58%.

The raw product of reaction was used as such in the next reaction.

On the raw product the following GLC/MS and $H^1$-NMR analysis were performed, allowing to assign the following parameters to the compound (VII)

$^1$H-NMR ($CDCl_3$), δ (ppm): 7.55–7.44 (2H, m, aromatic H) 7.01 (2H, m, aromatic H); 4.4–3.6 (1H, br s, —OH); 3–1.75 (8H, br m, H piperidinic ring); 2.59 (2H, q, J=7.3 Hz, ethylic —$CH_2$); 1.18 (3H, t, J=7.3 Hz, ethylic —$CH_3$). MS, m/z (%): 223 ($M^+$, 19), 208 (85), 190 (43), 122 (34), 109 (26), 95 (35), 94 (20), 84 (100), 71 (16), 57 (26), 56 (26).

B) Synthesis of 1-Ethyl-4-(p-fluororhenyl)-3-hydroxymethyl-1,2,3,6-tetrahydropyridine (II) [R=Et]

A solution of compound (VII) [R=Et] (10.0 g; 44.8 mmol) in aqueous $H_2SO4$ (40 ml water and 29.7 g $H_2SO_4$) was added with 4.0 g (49.3 mmoles) of a formaldehyde solution (37% in water), and was heat-refluxed under magnetic stirring for 6 hrs. The mixture was then cooled to room temperature, basified with 60.9 ml of a 30% aqueous solution of NaOH, and extracted repeatedly. The combined organic extracts were then washed once with water and concentrated.

The residue, in the form of a yellow-orange viscous oil, was diluted with 75 ml isopropanol and added with gaseous HCl in order to precipitate the hydrochloride of compound (II). The suspension thus obtained was filtered, washed with isopropanol, and the resulting solid was dissolved in water and added with NaOH 30% until pH 12 was reached. The resulting mixture was then extracted with toluene and the organic phase was evaporated. The compound (II) was thus obtained again 6.32 g), having HPLC purity >96% (Column Symmetry Shield RP8, eluent acetonitrile:buffer=90:10 ($KH_2PO_4$ 0.025 M at pH 2.5 with $H_3PO_4$), flow 1 ml/min, detector UV 215 nm). The yield of compound (II) was 60%. Compound (II) was characterised as follows:

m.p. 58–60° C.; $^1$H NMR($CDCl_3$), δ (ppm): 7.37–7.29 (2H, m, aromatic H); 7.01 (2H, t, J=8.6 Hz, aromatic H); 6.07 (1H, d, J=3 Hz, olephinic H); 5.2 (1H, br s, —OH); 3.89 and 2.60 (7H, m); 2.53 (2H, q, J=7 Hz, ethylic $CH_2$); 1.16 (3H, t, J=7 Hz, $CH_3$). MS, m/z (%): 235 ($M^+$, 29), 204 (100), 202 (36), 176 (21), 160 (21), 135 (37), 133 (39), 109 (85), 84 (17), 56 (68).

C) Synthesis of 4R cis- and 4R trans-4-(p-Fluorophenyl)-3-hydroxymethyl-1-ethylpiperidine (IIIa) and (IIIb) [R=Et], in the Presence of {RuCl(p-cymene)[(S)-BINAP]}$Cl^-$ Tetrahydropyridine (II) [R=Et] (35.5 g; 150.9 mmol) was hydrogenated in 300 ml isopropanol at a working pressure of 10 atm, at 120° C. in the presence of {RuCl(p-cymene)[(S)-BINAP]}$Cl^-$, previously generated by mixing a solution of (S)-BINAP (0.378 mmol, 0.235 g) in 21 ml of $CH_2Cl_2$:MeOH 1:1, with [$RuCl_2$(p-cymene)]$_2$ (0.188 mmol, 0.115 g), and heat-refluxing the mixture for 2 hrs. The reaction, controlled by GLC analysis of successive samples (capillary column AT-35), was discontinued after 2 hrs at 120° C. The resulting mixture was cooled to room temperature, filtered on Celite, and concentrated at reduced pressure to give 33.2. g of product (yield: 88%).

The crude product obtained was analysed by HPLC (Chiradex β-cyclodextrin Merck, eluent: methanol:buffer 15:85 (NaH2PO4 1.38 g/l, added with Na2HPO4 up to pH 6), flow 1 ml/min, Detector UV 215 nm) and the enantiomeric excesses were determined for both cis and trans diastereoisomers. The following results were obtained:

trans, ee ≧99%; cis, ee ≧99%. Cis/trans ratio: 55:45; overall ee ≧99%.

The cis and trans diastereoisomers were separated and characterised by MPLC purification on silica gel for analytical purposes.

4R-cis diastereoisomer had: m.p. 50–53° C. and $^1$H NMR ($CDCl_3$), δ (ppm): 7.44–7.20 (2H, m, aromatic H); 7.15–6.90 (2H, m, aromatic H); 5.8–4.5 (1H, br s, —OH); 3.9–1.6 (10H, m, piperidinic ring+hexocyclic $CH_2$); 2.25 (2H, q, J=7.2 Hz, ethylic $CH_2$); 1.13 (3H, t, J=7.2 Hz, ethylic $CH_3$). MS, m/z (%): 237 ($M^+$, 23), 222 (43), 206 (17), 133 (11), 114 (29), 109 (20), 84 (16), 72 (17), 58 (100).

4R-trans diastereoisomer had: m.p. 90–92° C. and $^1$H NMR ($CDCl_3$), δ (ppm): 7.3–7.1 (2H, m, aromatic H); 7.1–6.85 (2H, m, aromatic H); 3.5–3.0 (4H, m, piperidinic ring); 2.7–2.2 (4H, m, piperidinic ring+hexocyclic $CH_2$); 2.15–1.65 (5H, m, piperidinic ring+ethylic $CH_2$); 1.14 (3H, t, J=7.2 Hz, ethylic $CH_3$). MS, m/z (%): 237 ($M^+$34), 222 (76), 206 (16), 133 (14), 114 (34), 109 (27), 84 (21), 72 (22), 58 (100).

D) Synthesis of 4R-cis- and 4R-trans4-(p-Fluoroohenyl)-3-hydroxymethyl-1-ethylpiperidine (IIIa) and (IIIb) [R=Et], in the Presence of $Ru_2Cl_4$[(S)-BINAP]$_2$($NEt_3$)

Tetrahydropyridine (II) [R=Et] (5.0 g; 21.4 mmol) was hydrogenated in 40 ml isopropanol at a working pressure of 10 atm, at 120° C. in the presence of $Ru_2Cl_4$[(S)-BINAP]$_2$($NEt_3$), previously generated by adding (S)-BINAP and $Et_3N$ (0.032 ml) to a suspension of [$RuCl_2$(COD)]$_n$ (14.9 mg, 0.0531 mmol) in 2 ml toluene, heat-refluxing for 12 hrs, and evaporating the mixture to dryness. The reaction was discontinued after 5 hrs at 120° C., and the mixture was cooled to room temperature. After filtration on Celite, and evaporation under reduced lo pressure, 4.3 g of product (yield 84%) were obtained.

The enantiomeric excesses of both (IIIa) and (IIIb) diastereoisomers was determined by HPLC analysis (Chiradex β-cyclodextrin Merck, eluent: methanol:buffer 15:85 ($NaH_2PO_4$ 1.38 g/l, added with $Na_2HPO_4$ up to pH 6), flow 1 ml/min, Detector UV 215 nm). The following results were obtained:

trans, ee ≧99%; cis, ee ≧98%. Cis/trans ratio: 50:50; overall ee ≧99%.

E) Synthesis of 4R-cis and 4R-trans4-(D-Fluorophenyl)-3-hydroxymethyl-1-ethylipieridine (IIIa) and (IIIb) [R=Et], in the Presence of RuHCl[(S)-BINAP]$_2$ Tetrahydropyridine (II) [R=Et] (5.0 g; 21.4 mmol) was hydrogenated in 40 ml isopropanol at a working pressure of 10 atm, at 120° C. in the presence of RuHCl[(S)-BINAP]$_2$, previously generated by adding (S)-BINAP (74.0 mg, 0.120 mmol) and $Et_3N$ (0.017 ml) to a solution of [$RuCl_2$(COD)]$_n$ (14.9 mg, 0.0531 mmol) in 3 ml EtOH, heat-refluxing for 6 hrs, and evaporating the mixture to dryness. The reaction was discontinued after 5 hrs at 120° C., and the mixture was cooled to room temperature. After filtration on Celite, and evaporation under reduced pressure, 4.2 g of product (yield 83%) were obtained.

The enantiomeric excesses of both (IIIa) and (IIIb) diastereoisomers was determined by HPLC analysis (Chiradex β-cyclodextrin Merck, eluent: methanol:buffer 15:85 ($NaH_2PO_4$ 1.38 g/l, added with $Na_2HPO_4$ up to pH 6), flow 1 ml/min, Detector UV 215 nm). The following results were obtained:

trans, ee ≧99%; cis, ee ≧99%. Cis/trans ratio: 50:50; overall ee ≧99%.

F) Synthesis of 4R-cis and 4R-trans4-(p-Fluorophenyl)-3-hydroxymethyl-1-ethylpiperidine (IIIa) and (IIIb) [R=Et], in the Presence of Ru[(S)-BINAP](OAc)$_2$ Tetrahydropyridine (II) [R=Et] (5.0 g; 21.4 mmol) was hydrogenated in 40 ml isopropanol at a working pressure of 10 atm, at 120° C. in the presence of Ru[(S)-BINAP](OAc)$_2$ (48.0 mg, 0.057 mmol), previously generated, according to the method described in Inorg.Chem.27, 1988, 566–569, from [RuCl$_2$(COD)]$_n$ and (S)-BINAP. The reaction was discontinued after 18 hrs at 120° C., and the mixture was cooled to room temperature. After filtration on Celite, and evaporation under reduced pressure, 3.6 g of product (yield 71%) were obtained.

The enantiomeric excesses of both (IIIa) and (IIIb) diastereoisomers was determined by HPLC analysis (Chiradex β-cyclodextrin Merck, eluent: methanol:buffer 15:85 ($NaH_2PO_4$ 1.38 g/l, added with $Na_2HPO_4$ up to pH 6), flow 1 ml/min, Detector UV 215 nm). The following results were obtained:

trans, ee ≧43%; cis, ee ≧94%. Cis/trans ratio: 10:90; overall ee ≧89%.

G) Synthesis of 4R-cis and 4R-trans4-(p-Fluorophenyl)-3-hydroxymethyl-1-ethylpiperidine (IIIa) and (IIIb) [R=Et], in the Presence of Ru[(S)-BINAP](CF$_3$CO$_2$)$_2$ Tetrahydropyridine (II) [R=Et] (5.0 g; 21.4 mmol) was hydrogenated in 40 ml isopropanol at a working pressure of 10 atm, at 120° C. in the presence of Ru[(S)-BINAP](CF$_3$CO$_2$)$_2$ (50.0 mg, 0.031 mmol), previously generated from Ru[(S)-BINAP](oAc$_2$)$_2$ dissolved in CH$_2$Cl$_2$, added with trifluoroacetic acid, kept under stirring for 12 hrs, evaporated, re-dissolved in toluene and hexane and allowed to crystallise. The reaction was discontinued after 20 hrs, and the mixture was cooled to room temperature. After filtration on Celite, and evaporation under reduced pressure, 3.7 g of product (yield 73%) were obtained.

The enantiomeric excesses of both (IIIa) and (IIIb) diastereoisomers was determined by HPLC analysis (Chiradex βcyclodextrin Merck, eluent: methanol:buffer 15:85 ($NaH_2PO_4$ 1.38 g/l, added with $Na_2HPO_4$ up to pH 6), flow 1 ml/min, Detector UV 215 nm). The following results were obtained:

trans, ee ≧69%; cis, ee ≧93%. Cis/trans ratio: 34:66; overall ee ≧85%.

The results obtained by enantioselective hydrogenation are summarised in the following table:

| Complex | Yield (%) | ee (IIIa) (%) | ee (IIIb) (%) | Overall ee (%) |
|---|---|---|---|---|
| Example C | 88 | 99 | 99 | 99 |
| Example D | 84 | 99 | 98 | 99 |
| Example E | 83 | 99 | 99 | 99 |
| Example F | 71 | 43 | 94 | 89 |
| Example G | 73 | 69 | 93 | 85 |

It can be seen that the overall ee obtained was never below 85% in all tests; in particular, for the examples C, D, E, performed with preferred ligands and solvents, both the overall ee. and the specific (IIIa)- and (IIIb)-ee's were of 98–99%.

Example C was repeated with different alcoholic or halogenated solvents, in order to check the solvent effect on the enantioselectivity. The hydrogenation temperature was 120° C. and the reaction was discontinued after 5 hrs. The results are summarised in the following table.

| Solvent | Conversion (%) | ee (IIIa) (%) | ee (IIIb) (%) |
|---|---|---|---|
| CH$_2$Cl$_2$ | 62 | 98 | 99 |
| i-PrOH | 100 | 99 | 99 |
| n-PrOH | 59 | 95 | 98 |
| i-BuOH | 80 | 96 | 98 |
| Cyclohexanol | 93 | 98 | 96 |

As can be seen, all solvents afforded an ee of at least 95%. In the case of i-PrOH, in addition to an ee of 99%, a very high conversion rate (100% in 5 hrs) was observed.

H) Synthesis of 4R-cis- and 4R-trans4-(p-Fluorophenyl)-3-hydroxymethyl-1-ethyl-3-(3,4-methylenedioxyphenoxymethyl)piperidine (IV) [R=Et]

A 240 ml toluenic solution of the mixture of enantiomers (IIIa) and (IIIb) (40.0 g 169 mmol) obtained according to the preceding examples was mixed, at room temperature and under stirring, with triethylammine (1.7 equiv., 286 mmol, 21.0 ml), and subsequently with a solution of methansulphonyl chloride (1.2 equiv., 202 mmol, 15.6 ml) in toluene (40 ml) added dropwise over 1 hr.

The mixture was stirred at 25° C. for 3 hrs and filtered. The liquid phase was washed with water and the resulting organic phase was concentrated under reduced pressure. The residue (47.2 g) was dissolved in toluene (240 ml) and treated sequentially with a sesamol solution (1.0 equiv. in respect to the mixture of (IIIa) and (IIIb), 169 mmol, 23.3 g) in 4-methylpentan-2-ol (100 ml) and with an aqueous solution of NaOH 10 M (1.2 equiv. in respect to the mixture of (IIIa) and (IIIb), 201 mmol, 20.3 ml). The resulting heterogeneous mixture was heat-refluxed for 3 hrs. The reaction mixture was then washed three times with water until neutrality and the organic phase was separated. The aqueous phase was extracted again with toluene. The organic phases were combined and concentrated at reduced pressure. GLC analysis (SE-30 capillary column) of the viscous oil residue (55.0 g) revealed the presence of cis and trans diastereoisomers (IV) in a 10:90 ratio.

The residue was dissolved in isopropanol and added with gaseous HCl. Only the 4R-trans diastereoisomer (hydrochloride) precipitated in 74% yield (125 mmol; 49.1 g).

The hydrochloride was then re-converted into a free base by dissolution in water, basification with 30% NaOH, and extraction of the aqueous phase with toluene. The organic phase was evaporated to give the 4R-trans diastereoisomer free base (44.1 g). Yield: 99%.

The enantiomeric purity of said diastereoisomer determined by HPLC (Chiradex β-cyclodextrin Merck, eluent: methanol:buffer 40:60 (1% triethylammine with pH brought to 4.1 with AcOH), flow 1 ml/min, Detector UV 290 nm) was >99%.

NMR analyses carried out on AMX-600 BRUKER spectrometer including the recording of $^1$H and $^{13}$C spectra, 1H—1H COSY, Heteronuclear Shift Correlation, Heteronuclear Shift Correlation Long Range, and NOESY tests, allowed to assign the correct stereochemistry to the two reaction products. The product 4R-trans free base, a pale yellow syrup, has the following absorbances: $^1$H NMR (CDCl$_3$), δ (ppm): 7.16 (2H, m, H fluorophenyl); 6.96 (2H, m, H fluorophenyl); 6.62 (1H, d, J=8.8 Hz, H sesamol); 6.34 (1H, d, J=2.4 Hz, H sesamol); 6.13 (1H, dd, J=8.8 and 2.4 Hz, H sesamol); 5.87 (2H, s, O—CH$_2$—O); 3.58 (1H, dd, J=9.5 and 2.8 Hz, CH$_2$—O); 3.45 (1H, dd, J=9.5 and 6.8 Hz, CH$_2$—O); 3.31 (1H, m, CH—N); 2.45 (3H, m, ethylic CH$_2$+piperidinic CH); 2.20 (1H, m, piperidinic CH); 2.1–1.7 (4H, m, piperidinic CH); 1.17 (3H, t, J=7.2 Hz, CH$_3$). MS, m/z (%): 357 (M$^+$, 2), 220 (13), 205 (16), 137 (7), 109 (14), 98 (10), 82 (12), 72 (100), 58 (23).

I) Synthesis of Paroxetine Hydrochloride (I)

A solution of 4R-trans-4-(p-fluorophenyl-3-hydroxymethyl-1-ethyl-3-(3,4-methylenedioxyphenoxymethyl)piperidine (IV) [R=Et] (26.5 g; 74.1 mmol) in dichloromethane (135 ml) was cooled to 0° C. and added dropwise over 15 min is with a solution of phenylchloroformiate (22.6 g; 144 mmol) dichloromethane (22 ml). The clear yellow solution was maintained at room temperature for 3 hrs, and then washed with 150 ml of NaOH 1M and two portions of 150 ml HCl 6M. The organic phase was evaporated to dryness and re-dissolved with toluene (190 ml). The resulting mixture was then filtered and added with 19.2 g (343 mmol) of solid KOH and heat-refluxed for 2 hrs. The mixture was then cooled to room temperature and added with 150 ml water. The organic phase was separated and the aqueous phase was re-extracted with two portions of 100 ml water and evaporated to dryness.

The residue was dissolved in isopropanol (85 ml), and added with HCl 37%. Paroxetine hydrochloride was thus precipitated, filtered, washed and dried. 21.9 g (59.3 mmol) of paroxetin hydrochloride were thus isolated. This product, analysed by HPLC (Symmetry Shield RP8, eluent: acetonitrile:buffer 70:30 (KH$_2$PO$_4$ 0.025 M at pH 2.5 with H$_3$PO$_4$), flow 1 ml/min, Detector UV 290 nm) was found to have assay 99% and purity 99.9%, with yield 80%. Spectroscopic data were in accordance with literature data.

What is claimed is:

1. Process for the synthesis of paroxetine, comprising the following steps:

a) hydrogenation of a compound of formula (II), where R is a group selected from (C$_1$–C$_5$)alkyl, (C$_1$–C$_5$) carboxyalkyl, an optionally substituted phenyl, an optionally substituted benzyl, said hydrogenation being catalysed by a complex of a transition metal with chiral diphosphinic ligands, resulting in a 4R-enantiomerically enriched compound of formula (III):

b) reaction of the compound of formula (III) with a reagent capable of transforming the —OH group into a leaving group, followed by nucleophilic substitution with sesamol (3,4-methylenedioxyphenol), resulting in a 4R-enantiomerically enriched derivative of formula (IV):

c) N-dealkylation of compound (IV), resulting in paroxetine (I):

2. A process as claimed in claim 1, wherein R represents an ethyl.

3. A process as claimed in claim 1, wherein in said complex of a transition metal with chiral diphosphinic ligands, the transition metal is selected from the group consisting of ruthenium, iridium and rhodium.

4. A process as claimed in claim 1, wherein said complex of a transition metal with chiral diphosphinic ligands is a ruthenium complex selected from a compound of formula or a compound of formula {RuX(p-cymene)[BINAP]}X⁻, where X is a halogen atom; or a compound selected from RuHCl[BINAP]$_2$; Ru$_2$Cl$_4$[(BINAP]$_2$(NEt$_3$); Ru[BINAP](OAc)$_2$; Ru[BINAP](CF$_3$CO$_2$)$_2$, or a compound corresponding to one of the following formulas RuCl-p-cymene 5. A process as claimed in claim 1, wherein said complex of a transition metal with chiral diphosphinic ligands is prepared in situ in the hydrogenation mixture of step (a).

6. A process as claimed in claim 1, wherein said hydrogenation is carried out at a pressure of 1 to 150 atm, in an alcoholic or halogenated solvent or mixtures thereof, at a temperature of 60° C. to 150° C.

7. A process as claimed in claim 6, wherein said hydrogenation is carried out at a pressure of 5 to 15 atm and at a temperature of 100° C. to 130° C.

8. A process as claimed in claim 7, wherein said hydrogenation is carried out at a pressure of 10 atm and at a temperature of 120° C.

9. A process as claimed in claim 1, where said alcoholic or halogenated solvent used in step (a) is selected from dichloromethane, n-propanol, isopropanol, isobutanol, cyclohexanol, and their mixtures, and said complex of a transition metal with chiral diphosphinic ligands is a ruthenium complex selected from {RuCl(p-cymene)[(S)-BINAP]}⁻Cl, Ru HCl[(S)-BINAP]$_2$, Ru$_2$Cl$_4$[(S)-BINAP]$_2$(NEt$_3$).

10. A process as claimed in claim 1, wherein said reagent used in step (b), capable of transforming the —OH group into a leaving group, is added to compound (III) at a temperature comprised between −20° C. and +25° C. in the presence of an inert solvent and of a basic compound.

11. A process as claimed in claim 10, wherein said inert solvent is toluene and said basic compound is triethylamine.

12. A process as claimed in claim 1, wherein said reagent used in step (b), capable of transforming the —OH group into a leaving group, is selected from tosyl chloride, benzenesulphonyl chloride, methanesulphonyl chloride.

13. A process as claimed in claim 1, wherein said sesamol (3,4-methylenedioxyphenol) is added as a mixture with an alcoholic solvent in the presence of a base and the resulting mixture is heated for 2 to 4 hrs.

14. A process as claimed in claim 1, wherein said N-dealkylation in step (c) is effected by reacting the product (IV) with phenylchloroformiate, and treating the resulting product with a base.

* * * * *

UNITED STATES PATENT AND TRADEMARK OFFICE
CERTIFICATE OF CORRECTION

PATENT NO.    : 6,583,287 B1
DATED         : June 24, 2003
INVENTOR(S)   : Renzo Rossi et al.

It is certified that error appears in the above-identified patent and that said Letters Patent is hereby corrected as shown below:

The chemical formulas at Column 4, line 51 through Column 5, line 33 and Column 15, line 27 through Column 16, line 18, should appear as follows:

Signed and Sealed this

Second Day of March, 2004

JON W. DUDAS
*Acting Director of the United States Patent and Trademark Office*